United States Patent
Rose et al.

(10) Patent No.: US 6,692,731 B2
(45) Date of Patent: Feb. 17, 2004

(54) COMPOSITION FOR THE PERMANENT SHAPING OF HUMAN HAIR

(75) Inventors: Burkhard Rose, Darmstadt (DE); Jonathan Wood, Weinheim (DE)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 34 days.

(21) Appl. No.: 10/057,445

(22) Filed: Jan. 24, 2002

(65) Prior Publication Data

US 2002/0146378 A1 Oct. 10, 2002

(30) Foreign Application Priority Data

Jan. 26, 2001 (DE) ............................. 101 03 494

(51) Int. Cl.⁷ ................................. A61K 7/09
(52) U.S. Cl. ................... 424/70.2; 424/70.5; 514/944
(58) Field of Search ............... 424/70.2, 70.5; 514/944

(56) References Cited

U.S. PATENT DOCUMENTS

| 3,433,868 A | | 3/1969 | Brechner et al. .............. 424/47 |
| 5,904,919 A | * | 5/1999 | Brautigam et al. ........ 424/70.2 |

FOREIGN PATENT DOCUMENTS

| DE | 37 40 926 | 6/1989 |
| DE | 43 04 828 | 6/1994 |
| EP | 0 472 107 | 2/1992 |
| EP | 0 363 057 | 4/1994 |

* cited by examiner

*Primary Examiner*—Jyothsan Venkat
(74) *Attorney, Agent, or Firm*—Norris McLaughlin & Marcus

(57) ABSTRACT

A composition for the permanent shaping of human hair, with good waving capability while avoiding damage to the hair, comprises at least one reducing agent and 0.1% to 15% by weight, calculated to the total composition, of 2-methyl-1.3-propanediol.

5 Claims, No Drawings

COMPOSITION FOR THE PERMANENT SHAPING OF HUMAN HAIR

The present invention concerns a composition for the permanent shaping of human hair used both as a composition for the permanent waving of human hair with a good waving effect while nonetheless exerting no damaging influence on the hair, as well as for the straightening (smoothing) of curled hair.

It is generally known that permanent waving is carried out in two steps, the reductive splitting of the cysteine disulfide bonds in the hair by a reducing agent, and the subsequent neutralization by application of an oxidizing agent, whereby the cysteine disulfide bonds are restored.

The reducing agent still most frequently used today is thioglycolic acid, also in form of the salts thereof, in particular its ammonium salt, although numerous other thio compounds have been proposed for this purpose, which, however, mostly did not succeed.

The compositions containing thioglycollates are customarily applied at a pH-value between 7 and 10, in particular 8.5 and 9.5.

The present invention starts from the task of creating a composition for the permanent shaping of human hair which on the one hand shows good shaping capability while on the other hand reducing hair damage and which in particular can be used both as composition for the permanent waving of hair and as straightening composition, i.e. for the smoothing of kinky hair.

The solution of this task consists in adding to a shaping composition on aqueous basis, comprising at least one reducing agent and 2-methyl-1.3-propanediol in an amount between 0.1% and 15% by weight, preferably 0.25% to 10% by weight, in particular 0.5% to 5% by weight, calculated to the total composition.

Use of the various polyols as solvents as well as solubilizers and penetration agents in permanent waving compositions has been known for some time.

Thus, U.S. Pat. No. 3,433,868 already discloses two-phase permanent waving compositions with fast-breaking foam, which may additionally contain polyalcohols. Named as such are glycerol, 1.3-butylene glycol, propylene glycol, 1.2.6-hexane-triol, 1.5-pentanediol, 2-methyl pentanediol-2.4, 2-ethyl hexanediol-1.3 and various oligo- and polydiols.

EP 0 363 057 B1 concerns the use of 1.3-alkyl diols and 1.3-alkane diols in permanent waving compositions, preferably 2-ethyl-1.3-hexanediol and 1.3-butanediol.

However, use of these compounds fails to achieve a satisfactory effect; some, such as butanediols, can moreover cause skin irritation or sensitizing effects.

The permanent waving compositions according to the invention preferably comprise a reducing thio compound. Preferred are thioglycolic acid and thiolactic acid as well as the salts thereof, in particular the ammonium and ethanolamine salts.

Further useful thio compounds are in particular cysteine or the hydrochloride thereof, homocysteine, cysteamine, N-acetyl cysteine, thioglycerol, ethanediol monothioglycollate, 1.2-propyleneglycol monothioglycollate (see also WO-A 93/1791), 1-3-propanediol monothioglycollate or the isomer mixture resulting therefrom, 1.3-butanediol and 1.4-butanediol monothioglycollate and the isomer mixtures therefrom, polyethylene glycol, such as di-, tri- and tetraethyleneglycol monothioglycollates, glycerol monothiolactate and further thio acids and the esters thereof, as well as mixtures thereof.

The use of inorganic reducing sulfur compounds such as sodium hydrogen sulfite is basically also possible.

The total reduction agent content in the compositions according to the invention customarily amounts from 2.5% to about 15% by weight, calculated to the free thioglycolic acid as reference substance.

The waving compositions containing reducing agents can, if necessary, comprise alkalizing agents. Their quantity is dependent on the reducing agent and the desired pH-value of the composition. Reducing agent compositions preferably contain about 0.1% to about 5%, in particular about 0.5% to about 2.5% by weight thereof, calculated to the total composition.

Alkalizing agents preferred within the scope of the invention are ammonium carbamate, ammonia and/or ammonium(bi)carbonate. It is desirable to adjust the pH-value between about 6.5 and 9.5, preferably about 7 to 8.5.

The shaping compositions according to the invention are suited for use both for the permanent waving, i.e. curling of human hair and for the straightening, i.e. smoothing thereof.

The viscosity best suited for the permanent waving compositions according to the invention proved to be in the range of about 500 to 10,000 mPa.s, preferably about 1,000 to about 5,000 mPa.s, measured at 20° C. in a Brookfield viscosimeter (no. 5 spindle), whereas the viscosity suited for the straightening compositions is preferably higher in a range up to about 50,000 mPa.s, measured at 20° C. in a Brookfield viscosimeter (no. 5 spindle).

The viscosity is adjusted by addition of the appropriate amounts of thickening agents known per se, such as cellulose derivatives, polyelectrolytes, etc., or, preferably by the addition of $C_{10}$–$C_{22}$-fatty alcohols, in particular in admixture with long-chain quaternary ammonium compounds in a preferred amount of 1% to 15% by weight, in particular 2% to 10% by weight of fatty alcohol.

The permanent waving compositions used according to the invention preferably also contain surfactants. Their proportion ranges from about 0.1% to about 10%, in particular from about 1% to about 5% by weight of the composition containing the reducing agent.

The surfactants used both in the reduction agent compositions and in the neutralizer compositions are preferably the known products, which are optionally also used in combination.

Suitable anionic surfactants are especially the known alkyl ether sulfates and carboxylic acids, in particular in form of their alkali salts, as well as protein fatty acid condensates.

Suitable nonionic surfactants, which are preferred within the scope of the invention, are in particular $C_8$–$C_{18}$-fatty alcohol polyglycol ethers, fatty acid polyglycol esters, fatty acid alkanolamides, amineoxides, and especially $C_8$–$C_{18}$-alkyl polyglucosides.

Also possible is the incorporation of amphoteric surfactants, such as the known betaines and amido betaines, as well as, according to a further preferred embodiment, cationic surfactants, such as quaternary ammonium compounds, in particular in an amount from 0.05% to 5%, especially 01.% to 2.5% by weight, calculated to the composition containing the reducing agent.

Suitable long-chain quaternary ammonium compounds which can be used alone or in admixture are in particular cetyl trimethyl ammonium chloride, dimethyl dicetyl ammonium chloride, trimethyl cetyl ammonium bromide chloride, stearyl trimethyl ammonium chloride, dimethyl stearyl benzyl ammonium chloride, benzyl tetradecyl dimethyl ammonium chloride, dimethyl dihydrogenated tallow ammonium chloride, lauryl pyridinium chloride, lauryl dimethyl benzyl ammonium chloride, lauryl trimethyl ammonium chloride, tris-(oligooxyethyl) alkyl ammonium phosphate, cetyl pyridinium chloride, etc.

Suited are also the quaternary ammonium salts disclosed in EP-A 472 107.

Basically suitable are all quaternary ammonium compounds listed under the generic name "Quaternium" in the CTFA International Cosmetic Ingredient Dictionary, $4^{th}$ Ed. (1991).

In addition to 2-methyl-1.3-propanediol, a further component desirable in the reducing agent compositions used according to the invention are further mono and dialcohols or the ethers thereof, in particular mono-$C_1$–$C_3$-alkyl ether.

Preferred substances in this context are ethanol, n-propanol, isopropyl alcohol, 1-methoxypropanol(-2), 1-ethoxypropanol(-2) and ethoxydiglycol, preferably in an amount from about 0.1% to 10% by weight, calculated to the total composition.

Further diols and the esters thereof may also be used in subordinate amounts, for example, 1.3- and 1.4-butanediol, diethyleneglycol and the monomethyl and monoethyl ether thereof, as well as dipropylene glycol and the monomethyl and monoethyl ether thereof.

Glycerol, hexanetriol, ethyl carbitol, benzyl alcohol, benzyloxy ethanol as well as propylene carbonate (4-methyl-1.3-dioxolane-2-one), N-alkyl pyrrolidone and uria may also be used.

Further components additionally possible are cationic, anionic nonionic and amphoteric polymers, preferably in amounts of about 0.1% to about 5%, in particular about 0.25% to 2.5% by weight, calculated to the total composition.

The compositions used according to the invention can naturally comprise all the substances customarily found in permanent shaping compositions, a list of which will not be given here, and are preferably present as solutions, gels with a higher or lower viscosity, emulsions or creams.

They can be single-phase products or compositions packed into separate packaging which are united upon application, as they are disclosed, for example, in DE-C 43 04 828.

In order to avoid repetition, reference is here made to the state of the art as it is described, for example, in "Ullmann's Encyclopedia of Industrial Chemistry", Vol. A12 (1986), pages 588 to 591, and in particular to the monography of K. Schrader, "Grundlagen und Rezepturen der Kosmetika", $2^{nd}$. Ed. (1989, Hüthig Buchverlag) pages 823 to 840, as well as the article by D. Hollenberg et. al. in "Seifen-Öle-Fette-Wachse", 117 (1991), pages 81 to 87.

The compositions and individual components disclosed therein, to which express reference is made, can also be used within the scope of the present invention.

If desired, before applying the reducing agent it is also possible to apply a pre-treatment composition as disclosed, for example, in DE-A 37 40 926. After application of this pre-treatment composition, the hair is rolled onto curlers and the reducing agent composition is applied. After about 15 to 30 minutes processing and rinsing, the hair is neutralized with customary peroxide or bromate compositions, known as state of the art.

Between the reducing and the neutralizing phase it is also possible to apply an intermediate treatment known per se.

The following Examples illustrate the invention.

EXAMPLE 1

| Alkaline Permanent Wave for Normal Hair | |
|---|---|
| Ammonium thioglycollate (60%) | 21.3 (% by wt. |
| Ammonium hydrogen carbonate | 5.0 |
| 2-Methyl-1.3-propanediol | 3.0 |
| PEG-40-Hydrogenated castor oil | 0.7 |
| Polyquaternium-35 | 0.5 |
| Perfume | 0.4 |
| Ammonia, 25% | ad pH 8.3 |
| Water | ad 100.0 |

With this composition the hair was permanently waved for about 15 minutes, rinsed and neutralized for about 8 minutes with a customary 2.5% $H_2O_2$ composition. An emphatic permanent wave of appealing appearance was obtained. Substitution of the 2-methyl-1.3-propanediol by the same amount of 1.3-butylene glycol led to a wave with substantially weaker contours.

EXAMPLE 2

| Alkaline Permanent Wave for Damaged Hair | |
|---|---|
| Ammonium thioglycollate (60%) | 15.0 (% by wt.) |
| Ammonium hydrogen carbonate | 2.5 |
| Ceteth-20 | 0.7 |
| Tallow trimonium chloride | 0.1 |
| 2-Methyl-1.3-propanediol | 0.5 |
| Polyquaternium-6 | 1.5 |
| Perfume | 0.4 |
| Ammonia, 25% | ad pH 8.0 |
| Water | ad 100.0 |

The permanent wave achieved with this composition was similar to the one obtained with the composition according to Example 1.

Substitution of the 2-methyl-1.3-propanediol by 2-methyl-2.4-pentanediol led to waves with substantially weaker contours.

EXAMPLE 3

Neutral Permanent Wave for Normal Hair

A permanent waving product consisting of two Compositions A and B, filled into a two-chamber packaging the chambers of which were kept separate until application, was prepared by destruction of the separating wall and applied onto human hair rolled onto curlers. The hair was rinsed after about fifteen minutes processing and neutralized for about five minutes with a 2.5% $H_2O_2$ neutralizer composition, rinsed again, shampooed and dried.

An expressive, even, intensive permanent wave was obtained.

An identical treatment, to which, however, 0.5% by weight of 2-ethyl-1.3-hexanediol had been added in place of the same amount of 2-methyl-1.3-propanediol, showed a visibly inferior wave.

| Composition A: | |
|---|---|
| Ammonium hydrogen carbonate | 4.5 (g) |
| Polyquaternium-6 | 1.0 |

-continued

| Composition A: | |
|---|---|
| PEG-65-Hydrogenated castor oil | 0.8 |
| Isopropyl alcohol | 1.5 |
| Ethoxydiglycol | 2.0 |
| Cocoamidopropyl betaine | 1.0 |
| Perfume | 0.3 |
| Turbidifying agent | 0.5 |
| Ammonia, 25% | ad pH 8.4 |
| Water | ad 72.0 |

| Composition B: | |
|---|---|
| Ammonium thioglycollate, 70% | 18.0 (g) |
| Thiolactic acid | 2.0 |
| 2-Methyl-1.3-propanediol | 0.5 |
| Ammonia, 25% | ad pH 5.5 |
| Water | ad 28.0 |

After admixture of both Compositions a ready-to-use product with a pH-value of 7.4 was obtained.

EXAMPLE 4
Neutral Permanent Wave for Dyed Hair

A permanent waving product filled into a two-chamber package was prepared in analogy to Example 4:

| Composition A: | |
|---|---|
| Ammonium hydrogen carbonate | 3.5 (g) |
| Polyquaternium-11 | 0.5 |
| Ethanol | 0.5 |
| 1-Methoxypropanol (-2) | 1.0 |
| Cocoamidopropyl betaine | 1.0 |
| PEG-25-glyceryl cocoate | 0.8 |
| Perfume | 0.3 |
| Turbidifying agent | 0.5 |
| Ammonia, 25% | ad pH 8.3 |
| Water | ad 72.0 |

| Composition B: | |
|---|---|
| Ammonium thioglycollate, 70% | 13.0 (g) |
| Thiolactic acid | 0.5 |
| 2-Methyl-1.3-propanediol | 1.5 |
| Ammonia, 25% | ad pH 5.5 |
| Water | ad 28.0 |

A Product with a pH-value of 7.4 was obtained by admixture of the Compositions immediately prior to application.

After application onto dyed hair as described in Example 3, this mixture resulted in an expressive permanent wave, which had not effect whatever on the color gloss and color intensity.

EXAMPLE 5

| Alkaline Permanent Waving Gel | |
|---|---|
| Ammonium thioglycollate, 70% | 15.0 (g) |
| Ammonium hydrogen carbonate | 4.5 |
| PEG-40-Hydrogenated castor oil | 0.7 |
| $C_{12}$–$C_{18}$-Fatty alcohol mixture | 3.5 |
| 2-Methyl-1.3-propanediol | 0.5 |
| Polyquaternium-28 | 0.1 |
| Perfume | 0.3 |
| Ammonia, 25% | ad pH 8.0 |
| Water | ad 100.0 |

EXAMPLE 6

| Straightening Composition | |
|---|---|
| Thioglycolic acid | 8.0 (% by wt.) |
| $C_{16}$–$C_{22}$-Fatty alcohol mixture | 3.5 |
| Oleth-50 | 2.5 |
| Laureth-23 | 1.5 |
| Polyquaternium-2 | 0.8 |
| 2-Methyl-1.3-propanediol | 5.0 |
| Perfume | 0.6 |
| Monoethanolamine | ad pH 9.6 |
| Water | ad 100.0 |

This composition constitutes an effecting smoothing composition for kinky hair. None of the permanent waving or smoothing compositions according to the invention according to Examples 1 to 6 showed the slightest irritating or sensitizing effect, even upon repeated application.

What is claimed is:

1. Composition for the permanent shaping of human hair, comprising at least one reducing agent, wherein it comprises 0.1% to 15% by weight, calculated to the total composition, of 2-methyl-1.3-propanediol.

2. Composition according to claim 1, comprising 0.25% to 5% by weight, calculated to the total composition, of 2-methyl-1.3-propanediol.

3. Composition according to claim 1, comprising 0.1% to 5% by weight, calculated to the total composition, of at least one nonionic surfactant.

4. Composition according to claim 1, wherein it has a Brookfield viscosity of 500 to 10,000 mPa.s at 20° C.

5. Composition according to claim 1, comprising 0.1% to 10% by weight, calculated to the total composition, of 1-methoxypropanol and/or ethoxydiglycol.

* * * * *